United States Patent [19]
Power

[11] Patent Number: 5,365,065
[45] Date of Patent: Nov. 15, 1994

[54] SENSITIVE INTERFEROMETRIC PARALLEL THERMAL-WAVE IMAGER

[76] Inventor: Joan F. Power, 1100 Docteur Penfield, Appartment 822, Montreal, Quebec H3A 1A8, Canada

[21] Appl. No.: 17,273

[22] Filed: Feb. 12, 1993

[51] Int. Cl.⁵ .............................. G01J 5/08; G01J 5/00
[52] U.S. Cl. .................................. 250/330; 374/124; 356/432 T
[58] Field of Search ................ 374/124, 137, 129, 130; 250/330; 356/360, 345, 432 T

[56] References Cited

U.S. PATENT DOCUMENTS

| | | | |
|---|---|---|---|
| 3,909,132 | 9/1975 | Barrett | 374/130 |
| 4,306,150 | 12/1981 | Dietz | 250/332 |
| 4,634,870 | 1/1987 | Metcalf | 250/332 |
| 4,747,698 | 5/1988 | Wickramasinghe et al. | 374/124 |
| 4,985,858 | 1/1991 | Morrison, Jr. et al. | 374/129 |
| 5,072,120 | 12/1991 | Siewick | 250/330 |
| 5,102,231 | 4/1992 | Loewenstein et al. | 374/129 |

FOREIGN PATENT DOCUMENTS

| | | | |
|---|---|---|---|
| 0186826 | 8/1986 | Japan | 374/137 |
| 2207236 | 1/1989 | United Kingdom | 374/137 |
| 0789691 | 12/1980 | U.S.S.R. | 374/124 |

OTHER PUBLICATIONS

"An interferometric calorimeter for thin-film thermal diffusivity measurements", K. L. Saenger, J. Appl. Phys. 65(4), Feb. 15, 1989, pp. 1447–1452.

*Primary Examiner*—Diego F. F. Gutierrez
*Attorney, Agent, or Firm*—Michael, Best & Friedrich

[57] ABSTRACT

All spatial elements of the thermal-wave image generated in a heated material sample are detected simultaneously, or 'in parallel', in the invention by the use of an optical-wavelength interferometer whose sensing arm contains a combination of the heated material sample, contacted to a thermally conductive, optically reflective material layer, which is in turn contacted to a phase-shift medium comprised of an optically transmissive layer of condensed phase material through which the interferometer beam passes and is reflected by the optically reflective material layer. The invention thus converts a thermal-wave image into an optical wavelength interferometric image which can then be rapidly detected in parallel and with high sensitivity using a video-camera or other optical recording device. The invention is over one hundred times more sensitive than prior art interferometric instruments which use air as the phase-shift medium.

12 Claims, 3 Drawing Sheets

SENSITIVE INTERFEROMETRIC PARALLEL THERMAL-WAVE IMAGER

BACKGROUND OF THE INVENTION

This invention refers to a combination of a thermooptical phase shift means and an interferometer, where thermooptical refers to the change in the optical properties of a material medium caused by induced temperature changes in the medium.

A thermal-wave is an oscillating or transient temperature disturbance which propagates in a material medium. Thermal-waves are used in thermal-wave imagers which, in general, have powerful capabilities in comparison with most optical imaging instruments, such as microscopes, cameras, etc. For example, they can provide depth-dependent images of thin samples of materials to depths ranging from millimeters to nanometers. Thermal-wave imagers use methods of heating as follows:

a) Contact heating by conduction into the sample from an adjacent heated layer or other element such as a heated wire.

b) Direct heating of the sample layer by optical absorption and accompanying release of heat by this photothermal mechanism. This mechanism also includes heating with microwaves, and radio frequency fields, that is by the general absorption of electromagnetic radiation.

c) Radiative heat transfer from a blackbody heat source positioned accessibly to the sample.

d) Convective heat transfer from a heated fluid adjacent to the sample.

e) Internal heating by passing an electric current through conducting parts of the sample.

f) Heating by chemical reactions or phase changes occuring in the sample.

SUMMARY OF THE INVENTION

If the surface of the sample is heated with a sinusoidally modulated heat source, the temperature profile as a function of depth into the sample attenuates exponentially with depth, provided the sample is thermally homogeneous. The depth at which the temperature profile attenuates to a fraction of about 0.37th of the surface value is called the thermal diffusion length. The temperature profile, or thermal-wave, is then said to be critically damped with distance. The effective damping distance is given by the thermal diffusion length.

The thermal diffusion length $\mu$ depends on both the modulation frequency $\omega$ of the heat source at the surface of the sample, and the thermal diffusivity of the sample $\alpha$, where the latter is given by the following equation:

$$\alpha = k/\rho c_p \quad (1)$$

where k is the thermal conductivity $\rho$ is the density and $c_p$ is the specific heat of the sample.

The thermal diffusion length's dependence on the above variables is given by the following equation:

$$\mu = \left[\frac{2\alpha}{\omega}\right]^{1/2} \quad (2)$$

Equation 2 indicates that for a given sample, the effective depth of penetration of a thermal wave can be varied by changing the modulation frequency $\omega$ of the driving source, and this principle underlies the depth-profiling capabilities of thermal-wave imaging methods.

The depth profiling principle is used to recover depth-dependent images in several ways. First, if the sample is nearly thermally homogeneous, but has optically absorbing features at depths below the sample surface, light absorption by these features from a modulated optical source and subsequent heat release will cause these absorbing features to act as sources of thermal waves. The thermal waves from the buried sources diffuse a distance $\mu$, beyond which they are significantly damped. Therefore, only those features which lie at a significant depth which is less than or equal to $\mu$ will make a significant contribution to the temperature measured at the surface.

Consequently, if the surface temperature of the sample is scanned at a number of points, a thermal-wave image is produced having signal contributions from all of the subsurface heat sources which lie within a thermal diffusion length of the surface. Images acquired at low modulation frequencies will show the contributions of deeply buried heat sources, while images acquired at high modulation frequencies contain significant image contributions from the near surface region only.

Second, if the sample is optically opaque but thermally inhomogeneous, then, as the modulation frequency is decreased and a significant component of the temperature profile reaches buried thermal discontinuities or interfaces in the sample, these discontinuities will absorb or reflect the temperature profile, depending on the relative values of the thermal efflux of the two adjacent layers at the discontinuity or interface. The thermal efflux $\zeta$ at the interface is given by Equation 3:

$$\zeta = [k\rho c_p]^{1/2} \quad (3)$$

where k is the thermal conductivity, $\rho$ is the density, and $c_p$ is the heat capacity of the sample.

The absorption or reflection of the thermal wave by buried subsurface layers or discontinuities causes a change in the measured temperature at the sample surfaces, relative to the thermally homogeneous sample. By measuring the surface temperature at a number of points over the area of the sample, an image of the sample surface temperature may be reconstructed. This two-dimensional representation is referred to as a thermal-wave image.

Thirdly, and this is true for most materials, the sample may be both thermally and optically inhomogeneous. In this case, the depth profile mechanism will be a mixture of the mechanisms described in cases (1) and (2) above. The modulation frequency of the thermal wave remains the key factor in setting the sampling distance of the thermal-wave or waves.

So far, the recovery of depth-dependent, thermal-wave image recording has been discussed only for the case of samples excited by sinusoidal (or periodically) modulated heat sources. It is also possible to establish non-periodic or transient thermal-waves in a sample by using a time-varying heat source which is pulsed or stepped in time. The sampling depth of a transient thermal-wave is a function of the time between the application of the excitation and the time of observation. Depth resolved thermal-wave images may then be obtained by measuring the temperature at a number of points on the sample surface at a fixed time delay following the application of the heating transient excitation.

While there exist thermal-wave imaging methods which are capable of directly detecting the temperature distribution below a sample surface, most thermal-wave detection techniques record thermal-wave images by measuring a physical quantity which is proportional to, or related to the surface temperature of the sample. The surface temperature is measured at either the front or the rear surface of the sample.

As the modulation frequency of the heat source generating the thermal-waves in the sample is changed, the thermal-wave image then contains image information from different depths in the sample. The term 'depth' here refers to the distance from the sample surface which is nearest to the heat source. The surface of the sample located nearest to the driving heat source is called the 'front surface' while that furthest from it is called the 'rear surface'. Thermal-wave imaging methods which record images of the rear surface of the sample are referred to as 'transmission thermal-wave imaging methods'.

Most prior art thermal-wave imagers scan an image of the sample spatially on a point-by-point basis, that is they are said to be 'non-parallel'. In these methods, a focused heat source is scanned over the surface of the sample from point to point. Images may then be recorded at various frequencies as desired. Point-wise scanning is, however, a slow process, since large numbers of points on a surface must be scanned to build up an image of acceptable resolution. A few fast-scanning methods have been developed, but the depth-profile information recovered using these faster techniques is severely limited. Also, the time-scale of point-wise imaging methods varies from minutes to hours per image recovered.

These disadvantages of point-wise scanning are shared by other non-photothermal imaging techniques, for example, by Hadamard transform imaging, confocal scanning microscopy, confocal Raman microprobe analysis, and so on. The fastest methods of imaging require that all points of the image on the surface be detected simultaneously, or 'in parallel' as it is called. Photography is a classic example of a parallel image detection method.

Parallel thermal-wave imaging is the only means of producing thermal-wave images that can be detected and displayed at very high resolution on a time scale of milliseconds or less. This short time scale is required for the imaging technique to be useful as a routine diagnostic or observational tool, since it is close to the response time of a human observer. The utility of an imaging technique decreases steadily with lengthening of the image detection time, because the relative number of samples that can be inspected or studied decreases as the measurement time increases.

Only a few parallel instruments have so far been developed for thermal-wave imaging. These methods use techniques which measure temperature changes in samples, or in an adjacent medium, by optical means. Specifically, the thermal information must be encoded on an optical beam or on an optical radiation field. The spatial elements of the image are carried by this optical beam or field, with preservation of the spatial interrelationships. A visible or infrared videodetector, such as a vidicon, electrooptic camera, photodiode array, or infrared video-camera is typically used to record such an image, ensuring rapid image recovery.

Such prior art parallel detection methods in thermal-wave imaging may be summarized as: (1) infrared, thermal-wave video-radiometry, (2) parallel, photopyroelectric effect radiometry, and (3) surface-detected photothermal interferometry.

Parallel infrared video-radiometry (1) uses wide area sample heating to produce temperature changes in the sample. Radiative heat loss occurring from the heated sample then produces blackbody infrared emission according to the Stefan-Boltzmann law. A spatial temperature distribution in the sample produces a spatially distributed field of infrared radiation from the sample, due to the blackbody emission. For small induced temperature changes in the sample, the intensity of the black body emission is linearly or directly proportional to the induced change in temperature. The spatial temperature distribution in the sample (which defines the thermal-wave image) is thereby encoded into a proportional infrared radiation image which can be detected using an infrared camera. If the induced temperature change is not small, the infrared emission intensity is no longer directly proportional to the temperature change. The image information is then said to be non-linear. Although then more difficult to interpret, it is still usable and is recorded by the infrared camera.

The main disadvantages of infrared video-radiometry are its low sensitivity and the long radiation wavelengths associated with the blackbody emission from samples at temperatures around the ambient values. The sensitivity is low because the blackbody emission process is optically incoherent, and therefore emitted radiation intensities are low per unit induced temperature change. Also, infrared detectors tend to be insensitive devices. An additional disadvantage is that the image resolution (smallest detectable surface feature separation) is poor, due to the fact that mid-infrared radiation is detected by the camera, so that the best resolution limit for imaging is fixed at a few microns or greater by the Rayleigh criterion.

Parallel, photopyroelectric effect radiometry (2) places a sample in thermal conductive contact with a thin fill of pyroelectric sensing material. The sample is then heated by a heat source broadfield, and heat is conducted through the sample layer to the pyroelectric by conduction. As the average temperature in the pyroelectric changes, a voltage is produced across the pyroelectric layer which is linearly proportional to the said average temperature change. A spatially distributed temperature change is induced in the sample layer, and this in turn induces a linearly related spatially distributed change in the average temperature of the pyroelectric, which then produces a spatially varying voltage across the pyroelectric layer. This transfers the thermal-wave image in the sample layer into a spatially dependent voltage change in the pyroelectric sensor.

In this method, parallel image recording requires the use of an array of sensing pins or contacts, spatially distributed behind the heated sample. The contacts or pins sample the electric field distribution which is produced in the pyroelectric by the heating. This has the disadvantage that (a) the image resolution is set by the spatial distribution of the sensing pins, (b) no means exists for changing the scale of the image resolution without changing the positioning of the pins, (c) specialized electronic detection circuits must be employed if the thermal-wave image formation is to be averaged electronically over time, (d) the frame-readout process is ordinarily slow.

Previously interferometry (3) has only been used to generate surface images in the air or other gas adjacent to the sample's surface. A sample to be studied or imaged is heated in air with a laser beam, for example. This surface heating causes (a) a volumetric expansion on the sample surface, thereby producing a so-called 'thermal bump' on the surface, (b) heat flows into the layer of air next to the sample surface causing a change in the refractive index of the air. Effects (a) and (b) together produce a change in the optical path length, and this is detected by a fringe shift in an interferometer.

For example, on one previous instrument, the heating beam was defocussed to irradiate the sample surface in a broad-field or diffuse manner; the interferometer beam impinged on the entire heated surface of the sample and a parallel image was recovered by means of a photographic plate or camera. This prior art had the disadvantage that the detection of the thermal effect was in the air layer next to the sample surface and was very insensitive as a result. This is so for two reasons: (1) the temperature coefficient of refractive index (denoted by dn/dT) is several hundred times smaller in air than in most solid or liquid media or layers; therefore, the thermally induced phase-shift to be detected is much smaller in air or gas than when a solid layer is used, as in the present invention; (2) relatively little of the heat used to heat the sample is conducted back into the adjacent air or gas. For most solids, 99.9% of the thermal energy is reflected back into the solid itself at an air-to-solid interface, and only 0.1% of the generated thermal energy is this transmitted back out of the solid to the air adjacent to form the thermal image.

The temperature-dependent, optical phase shift, which is the desired signal, is given by Equation 4 for a uniformly heated layer of thickness l:

$$\Delta\phi = (2\pi/\lambda)[\partial n/\partial T]\Delta Tl \qquad (4)$$

where $\Delta\phi$ is the phase shift, n is the refractive index, $\lambda$ is the wavelength, T is the temperature, $\partial n/\partial T$ is the gradient of refractive index with temperature and $\Delta T$ is the temperature rise in the air layer next to the solid heated sample. Typically $(\partial n/\partial T)$ is about $10^{-6}$ to $10^{-5}$ per K° in gases such as air, rising to $10^{-3}$ to $10^{-4}$ in most solids and liquids. We shall see that the signals produced in the prior art configurations are several orders of magnitude less than or weaker than in the present invention.

Turning now to a description of the invention: it comprises the conversion of a thermal wave image generated in a heated sample into an optical image which can then be rapidly recorded at high sensitivity and high resolution on a variety of available cameras or image recording means.

The invention comprises the following elements, each of which is in turn then described in more detail:
1) Heat is generated in a sample, thereby establishing a thermal-wave in the sample which carries the thermal-wave image information.
2) The thermal-wave propagates through the sample by conduction and into a thin layer of optically reflective but highly thermally conductive material called the reflector layer.
3) The thermal-wave propagates through the reflector layer and into a condensed-phase medium which is in thermal conductive contact with the reflector layer. This condensed phase medium is called the phase shift medium (PSM).
4) The phase shift medium (PSM) changes temperature as the thermal-wave propagates through it. The change in temperature of the PSM produces an optical phase shift in the probe beam of an interferometer also passing through the PSM, because of a change in the refractive index of the PSM caused by the heating.
5) The probe beam is propagated through the PSM from an interferometer and the said refractive index change in the PSM produces an optical phase shift in the probe beam of the interferometer.
6) The reflector layer optically reflects the interferometer probe beam incident on its surface, and causes the said probe beam to pass twice through the PSM, traversing the PSM along and approximately coincident with the optical axis of the incident probe beam at the reflector layer, but exiting the PSM in a direction opposite to the direction of propagation of the incident probe beam.
7) The phase shift in the optical probe beam is measured using an interferometer, thereby producing an interferogram from which the optical phase shift may be reconstructed.
8) The interferogram is recorded by means of an electrooptic camera or other suitable recording means.

The said heating of the sample is achieved by optical absorption with subsequent evolution of heat, or by radiative heating, or by electrical heating, or by other means. In the preferred embodiment, the heating mechanism is by optical absorption with subsequent evolution of heat.

The combination of the heated sample in thermal contact with the reflector layer, and with the thin reflector layer in thermal conductive contact with the phase shift medium (PSM) comprises a thermooptical phase shift element (TPSE). As described below, the TPSE converts a thermal-wave image of the sample into a two-dimensional distribution of optical phase variation on the probe beam which propagates through the TPSE. Furthermore, the TPSE achieves this conversion with high sensitivity.

The TPSE puts the heated sample in thermal contact with the reflector layer. In a preferred embodiment, the sample is placed in thermal conductive contact with the reflector layer. However, the invention does not preclude the use of radiative or convective thermal contact between the sample and the reflector layer which could be employed if desired in some applications.

The reflector layer must be highly reflective at the optical frequency of the interferometer probe beam. It must also be a good thermal conductor so that heat is efficiently conducted through it. Both requirements are satisfied using a thin film of metal as the reflector layer. The function of the reflector layer is twofold: first, it functions as a mirror for the probe beam, confining it to the interferometer. Second, it acts as a beam stop for any optical radiation produced by the heating beam, in the case where an optical radiation beam is used for the heating, functioning, in this case, to prevent any of this outside optical radiation from the heat source from entering the interferometer.

The phase shift medium (PSM) is composed of a material possessing a large temperature coefficient of refractive index at the frequency of the probe beam used in the interferometer. The PSM must also be of a material which optically transmits radiation at the probe beam's optical frequency.

As heat is conducted through the sample and through the reflector layer into the PSM, the temperature in the PSM changes, as given by Equation 5, which relates the change in refractive index of a uniformly heated layer with small change in temperature:

$$\Delta n = [\partial n/\partial T]\Delta T \qquad (5)$$

where $\Delta T$ is the change in temperature of the layer, $\partial n/\partial T$ is the temperature coefficient of the layers's refractive index, and $\Delta n$ is the change in refractive index n of the layer which is caused by the heating. The temperature coefficient of refractive index, $\partial n/\partial T$ should therefore be large at the optical frequency of the probe beam.

The thermooptical phase shift element, in addition to recording the refractive index change from heating, also functions as the sensing arm of the interferometer. The interferometer probe beam propagates through the PSM of the thermooptical phase shift element (TPSE), is then reflected by the reflector layer inside the TPSE, and then retraces its path through the PSM back along the incident optical path.

In its double-path propagation through the PSM, the probe beam experiences a change in the optical phase due to the temperature-induced refractive index change in the PSM. This optical phase change is expressed by Equation 6:

$$\Delta\phi(x,y) = (4\pi/\lambda)\int_0^l \Delta n(x,y,z)dz \qquad (6)$$

where n(x,y, z) is the thermally-induced distribution of the refractive index change in the phase shift medium, z is the direction which coincides with the axis of propagation of the optical beam propagating through the phase shift medium, $\lambda$ is the wavelength and x and y are coordinate axes which are orthogonal to the z direction of the probe beam propagation (as it is measured at the reflector layer). Coordinates x and y are referred to as the transverse coordinates, and the 'transverse dependence' of a quantity, such as optical phase shift or refractive index change, is assumed to be the said quantity's variation in the x and y directions. The three dimensional change in refractive index of the PSM caused by the spatially-dependent thermal-wave may be evaluated by Equation 7:

$$\Delta n(x,y,z)=[\partial n/\partial T]\Delta T(x,y,z) \qquad (7)$$

where the directions x,y,and z have the same orientation as in Equation 6.

The two-dimensional optical phase-shift change induced in the interferometer probe beam $\Delta\phi(x,y)$, which is given by Equation 7 is related to the spatial average of the three-dimensional temperature change $\Delta T(x,y,z)$ along the z axis, as described above. Equation 6, in combination with Equation 7, illustrates how the thermooptical phase shift element (TPSE) converts the transverse dependence of the temperature field in the PSM into a transverse, optical phase shift. Finally, the transverse dependence of the temperature field is related to the transverse dependence of the temperature field at the rear surface of the sample, this said physical quantity constituting the thermal-wave image information from the sample. Therefore, the TPSE converts a thermal-wave image of the sample, expressed by the temperature field, into an optical phase image in the interferometer, expressed by the phase shift distribution $\Delta\phi(x,y)$ in the interferometer probe beam.

The optical interferometer beam, on its path through the TPSE, has its phase shifted thermally according to the quantity $\Delta\phi(x,y)$. The thermal-wave image information from the heated sample is, therefore, transversely encoded on the electromagnetic field distribution of the interferometer beam. An interferometer records this transverse (x,y) dependence by superimposing the phase-perturbed optical beam which propagates through the TPSE with a reference beam or beams having coherence with respect to the probe beam which propagates through the sensing arm of the interferometer. There is no strict requirement that the optical source which supplies the interferometer probe beam be coherent. An incoherent optical source may be used if desired. There is also no strict requirement that the probe beam frequency should lie in the visible frequency range; it could, in principle, have a frequency lying anywhere in the range from the far-ultraviolet to the infrared. There is no strict requirement that the probe beam be a single frequency or ultra-narrowband. A probe beam comprised of a band of optical frequencies may be used for detection. There is, moreover, no strict requirement that the probe beam be plane; it may be focused prior to irradiation of the TPSE. In the preferred embodiment, the probe beam is coherent and narrowband, and lies in the optical frequency range; it is also assumed to be collimated, so that the optical phasefronts are nearly flat and so that the beam obeys planewave propagation laws, to a good approximation.

The interferometer used for detection may be any one of a variety of designs. The Twyman-Green design is the most suitable for inspection of surface areas having dimensions of a square millimeter or so or larger. The use of holographic recording gives enhanced preformance, but is not essential to the invention, provided that the stability of the instrument can be assured by appropriate design procedures. Other interferometers which may be used in the invention include the Newton and the Michelson types. A variety of polarization interferometers may be used for detection of the phase shift in the optical probe beam in the invention.

The interferogram produced by the interferometer may be detected and recorded by a wide variety of different types of cameras, including electrooptic cameras, vidicons, etc.

BRIEF DESCRIPTION OF THE VIEWS OF THE DRAWINGS

Figure 1:
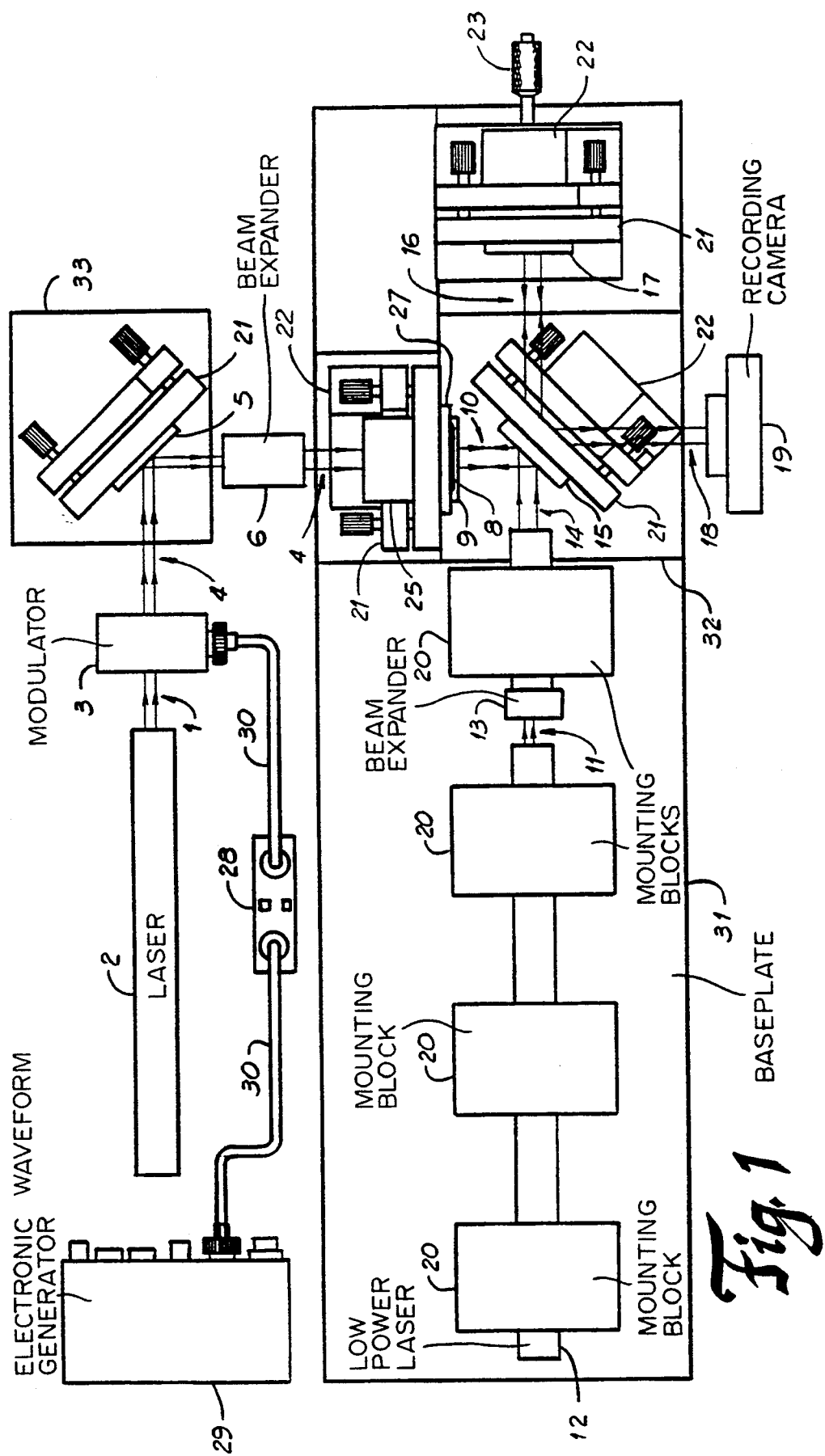
Figure 2:
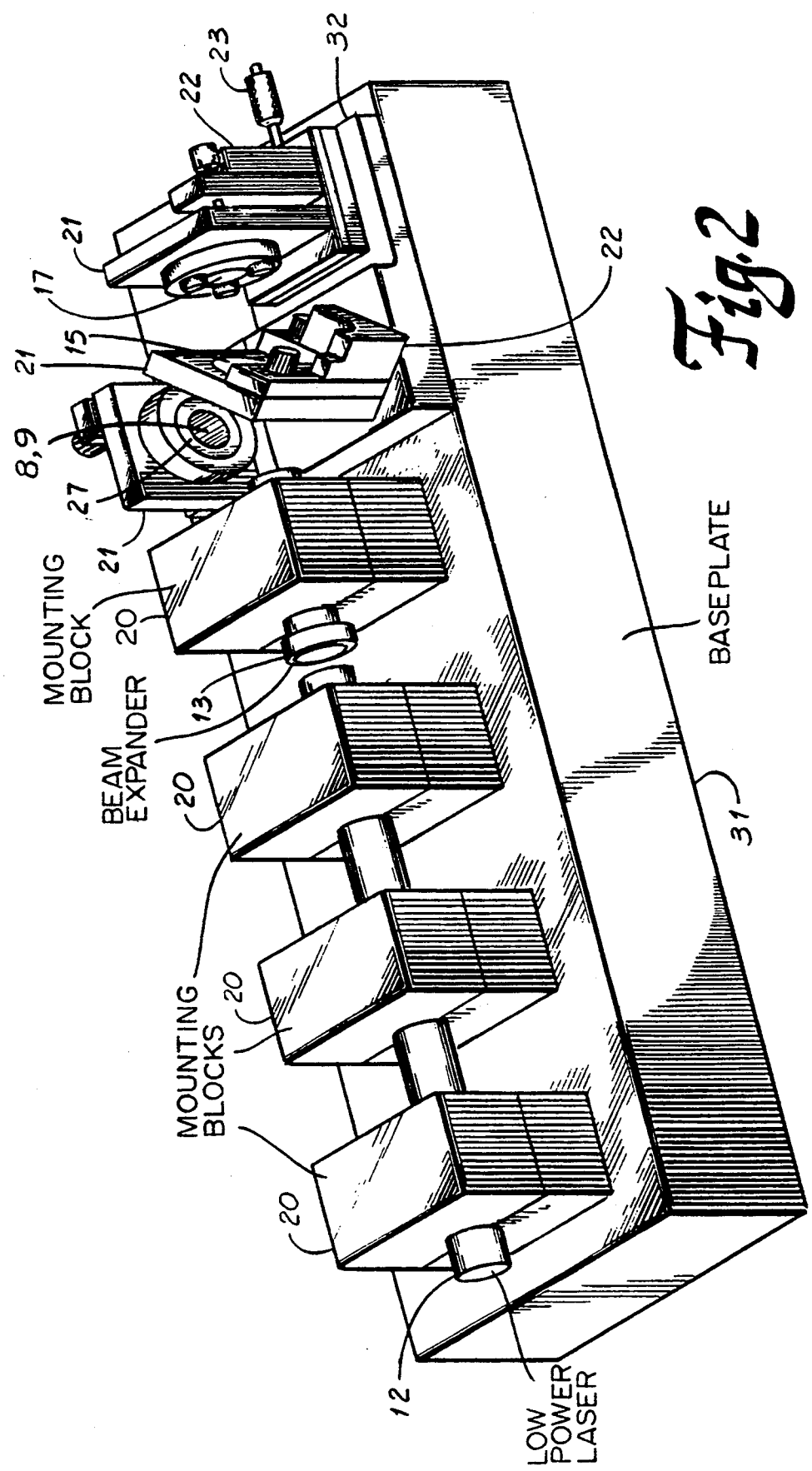
Figure 3:
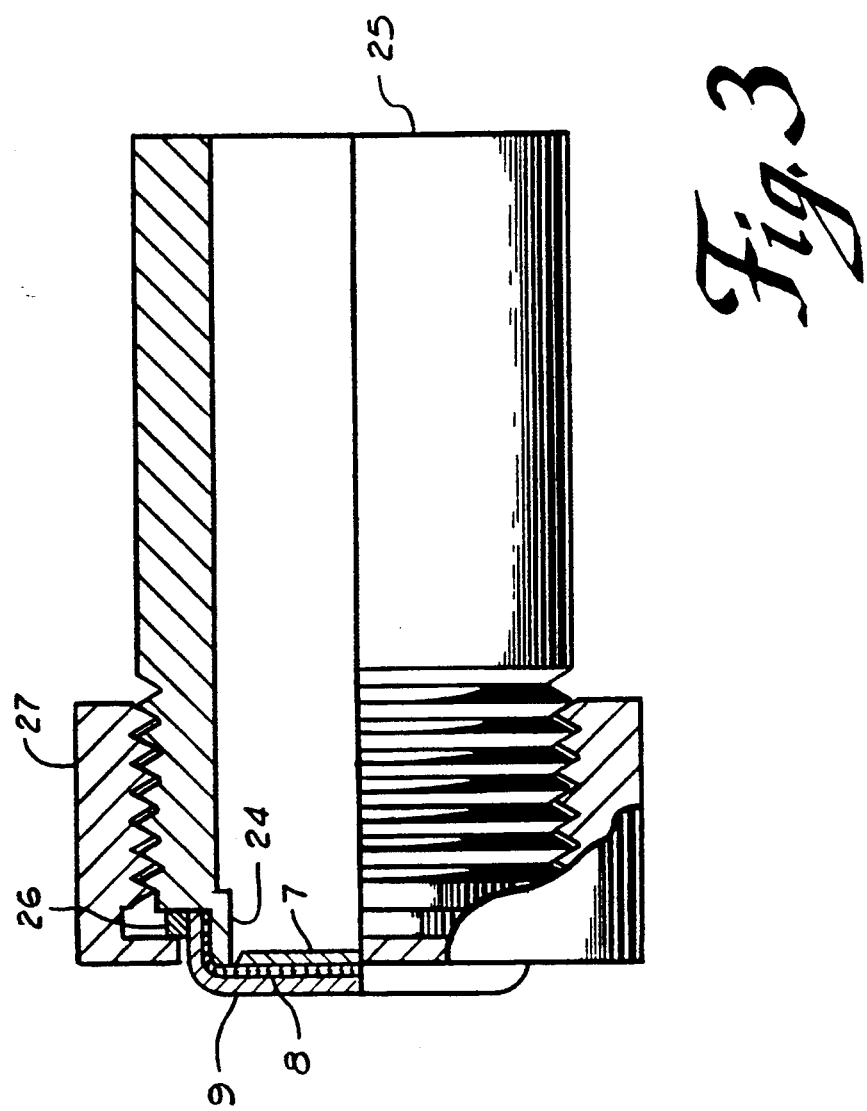

Having thus described the invention in general, we now describe a preferred embodiment with reference to FIGS. 1, a plan view, FIG. 2, a view of the interferometer assembly, and FIG. 3 showing details of the TPSE assembly.

DETAILED DESCRIPTION OF THE PREFERRED EMBODIMENT OF THE INVENTION

An optical (either visible or infrared) heating or excitation beam 1 from a laser optical radiation source 2 is directed through a modulator 3 which varies the intensity of the heating beam with time. The time-varying heating beam 4 is reflected by a plane mirror 5 and directed through an optional beam expander 6, and strikes the sample to be examined 7. Absorption of the excitation radiation by the sample 7 generates heat in the sample 7. The sample 7 is coated onto one side of a metallic reflector layer 8. On its opposite side the reflector 8 is coated with or contacted to a film of phase shift material 9 whose temperature coefficient of index of refraction at the wavelength of an interferometer sampling beam 10 is chosen to be as large as possible for maximum sensitivity. The combination of the sample 7, the reflector layer 8 and the phase shift medium 9 is called a thermooptical phase shift element (TPSE) ( See FIG. 3) because the heating of the phase shift medium 9 involves a change in its index of refraction, so that an interferometer sampling beam 10 entering the phase shift medium 9 and them being reflected back through it by the reflector layer 8 experiences an optical phase shift.

The interferometer beam 11 originates in a low power laser 12, passes through a beam expander 13 focussed approximately at infinity. The expanded beam 14 strikes a beamsplitter 15 where it is split into two beams of nearly equal intensity propagating along two paths which are mutually at right angles. The expanded beam is split into two beams at the front surface of the beam splitter 15, where 'front' refers to the beam splitter surface which is positioned closest to the low power laser 12. The first of these two beams is called the reference beam 16. It travels through the beam splitter 15, strikes a movable plane mirror 17 and then returns to the beam splitter 15. The second of the two beams 10 is called the interferometer sampling beam. The sampling beam is reflected at the front surface of the beam splitter 15 and directed along a path at right angles to the incident beam 14. It strikes the thermooptical phase shift element ( TPSE 7,8,9) (FIG. 3), where it passes into the phase shift medium 9, strikes the reflector layer 8, is reflected back to pass through the phase shift medium 9 a second time and returns to the front surface of the beam splitter 15 where it is superimposed with the reference beam 16. These two beams are now out of phase because of the heating of the phase shift medium which is in thermal contact with the heated sample 7, and so an interference pattern or interferogram results on the front surface of the beam splitter 15, and this interferogram now contains the thermal-wave image information from the heated sample, as desired. The interferometer output beam 18 carries this interferogram to a recording camera 19, where the interferogram is detected in parallel.

The assembly, consisting of the interferometer optics 13,15,17, the TPSE elements 7,8,9,24,25,26,27, and the low power laser 12, is mounted on a baseplate 31. The low power laser 12 is further supported by mounting blocks 20, as is also the interferometer beam expander 13. The beam splitter 15, TPSE assembly 7,8,9,24,25,26,27, and interferometer plane mirror 17 are held in position using kinematic mirror mounts 21. These kinematic mirror mounts are bolted onto mounting blocks 22 which are designed to hold the knematic mirror mounts stably in position with a maximum aperture available for the interferometer beams 16, 10, 14, and 18. The mounting stage 22 used by the reference plane mirror is equipped with a micrometer adjustment 23 which is used as an adjustment to balance the interferometer. The mounting blocks 22 for the beam splitter and reference mirror 17 are secured to a common baseplate 32 which is attached to the main baseplate 31. The excitation plane mirror 5 is also mounted on a similar kinematic mirror mount 21 and is secured to a baseplate 33.

The TPSE assembly is shown in more detail in FIG. 3. It consists of the sample 7 deposited on the reflector layer 8 and the phase shift medium 9 which consists of an optically transparent thin film. This combination of elements 7, 8 and 9 is stretched over a flange 24 on a threaded shaft 25. A slip ring 26 pulls the film comprised of 7,8 and 9 taut over the flange and a tapped retainer cap 27 is screwed onto the shaft securing the slip ring 26 in position. The excitation beam 7 is directed into the shaft at the end opposite the flange 24. The TPSE assembly (7,8,9,24,25,26,27) is positioned in the interferometer using a kinematic mirror mount 21 which is in turn supported by an interferometer mounting block 22.

The modulating element 3 used to modulate the excitation beam 1 is shown in FIG. 1 as being of the acoustooptic type. The modulator element 3 requires a power amplifier unit 28 to supply the required electric signals to operate the modulator. The modulating signal which determines the pattern of time variation of the excitation beam 1 in the modulator is obtained from an electronic waveform generator 29 which is connected to the power amplifier unit 28 by means of a coaxial cable 30. Coaxial cable 30 is also used to connect the power amplifier unit 28 to the modulator element 3.

The invention thus has replaced the single, fixed mirror of the classical Twyman-Green interferometer with the thermooptical phase shift element (TPSE) and thereby converts a thermal wave-image in the sample to a form that can be displayed and recorded with the desired high sensitivity of an interferometer. The invention is thus a thermal-wave interferometric imager. In place of the Twyman-Green interferometer, the Newton or Michelson interferometers can also be employed if the TPSE is introduced into the appropriate adjustable arm of these interferometers.

Turning now to the advantages of the present invention over the prior art, these are summarised as follows: (1) the image generation is parallel so that all elements of the image are detected simultaneously; (2) the detection method is highly sensitive due to the novel combination of the thermooptical phase shift element and an interferometer to produce an interferogram; (3) the invention converts thermal-wave information to visible or optical image information which is much more easily detected and recorded.

The parallel image generation mechanism has a great advantage over all forms of scanned, thermal-wave imaging, thereby eliminating the long image-recovery times associated with the prior art, which severely limited their use as general diagnostic imaging methods.

The invention has much more sensitive image detection capabilities than either infrared video-radiometry or the conventional prior art methods of interferometry that have been discussed above. The sensitivity of infrared video-radiometry is limited because of the intrinsically low efficiency of blackbody emission; the use of interferometry is intrinsically more sensitive.

The use of a thermooptical phase shift element in combination with interferometry improves the sensitivity beyond that obtained with prior art interferometry which uses only air above the heated sample surface, or with interferometric detection of the volumetric displacement of the sample surface by the heating. The thermooptical phase shift element gives approximately two orders of magnitude greater change in temperature than just the use of an air layer adjacent to the sample surface, and the TPSE also has a temperature coefficient of refractive index which is approximately two to three orders of magnitude greater than that of air. The enhanced temperature change in the TPSE compared with air, plus the very large temperature coefficient of refractive index of the TPSE phase shift medium combine to produce a thermally-induced, optical phase shift in the interferometer probe beam which is several orders of magnitude greater than would be observed if the TPSE were absent and the refractive index change were observed in air alone, as was the case for the prior art methods which used only standard interferometry without the TPSE.

The conversion of thermal to visible wavelength, optical image information is an important improvement and part of the invention which is not shared by infrared video-radiometry. The detection of visible wavelength images gives an image-resolution which is below 1 micron, based on the optical diffraction limit. In infrared videoradiometry, the image resolution limit is in the range of only microns to tens of microns because the blackbody radiation used is emitted at these longer wavelengths. Also, the visible wave-length detectors used by the invention are orders of magnitude more sensitive than the infrared detectors used in the prior art infrared video-radiometry The optical image detection used in the present invention gives it an important advantage over the parallel, photopyroelectric imaging method. The recovery of images made by the photopyroelectric effect image method requires the use of a specialised array detector to sample the electric field at the rear surface of the heated sample; the image resolution is fixed by the dimensions of the sampling pins or elements in the array, and auxiliary optics cannot be used to scale the image and produce high resolution.

While the preferred embodiments of the invention have been shown and described, it will be obvious to those skilled in the art that changes and modifications may be made without departing from the spirit of the invention, the scope of which is defined by the appended claims.

I claim:

1. A parallel, thermal-wave imaging apparatus for obtaining a thermal-wave image of a material sample, said apparatus comprising:

heating means for heating the material sample and establishing a thermal-wave therein;

an interferometer having a probe beam and a reference beam;

a thermooptical phase-shift element including three contiguous layers mounted on a base and comprising the material sample as a first layer, an optically reflective and thermally conductive second layer, and an optically transmissive, optical phase-shift third layer, wherein the thermal-wave established in said material sample first layer is propagated through said second layer and to said third layer, said third layer being selected to induce an optical phase-shift in said probe beam of said interferometer, the optical phase-shift resulting from a variation in optical properties of said third layer as the thermal-wave is propagated in said third layer;

said probe beam of said interferometer being directed towards said thermooptical phase-shift element and entering through said third layer, reflecting on said second layer and returning through said third layer with an optical phase-shift, wherein said interferometer can detect the optical phase-shift and can establish an interferogram by comparison of the phase-shifted probe beam and the reference beam; and parallel recording means for detecting and recording at once a plurality of points on the sample to establish said interferogram which contains the thermal wave image information of the sample from which the thermal wave image is obtained.

2. An apparatus as in claim 1 wherein said interferometer is a Twyman-Green interferometer.

3. An apparatus as in claim 1 wherein said interferometer is a polarization interferometer.

4. An apparatus as in claim 1 wherein said recording means is a camera.

5. An apparatus as in claim 4 wherein said recording means is an electrooptical camera.

6. An apparatus as in claim 4 wherein said recording means is a vidicon.

7. An apparatus as in claim 1 wherein said heat source time-varied in intensity.

8. An apparatus as in claim 1 wherein said second layer is a thin metallic layer.

9. An apparatus as in claim 1 wherein said third layer consists of a material possessing a large temperature coefficient of refractive index greater than $10^{-5}$ per °K at the frequency of the interferometer's probe beam.

10. An apparatus as in claim 9 wherein said third layer is an optically transparent film.

11. An apparatus as in claim 9 wherein said third layer is a condensed-phase material.

12. A method of parallel, thermal-wave imaging of a material sample, said method comprising:

(1) heating the material sample and establishing a thermal-wave therein;

(2) providing a thermooptical phase-shift element including three contiguous layers mounted on a base and comprising the material sample as a first layer, an optically reflective and thermally conductive second layer, and an optically transmissive, optical phase-shift third layer;

(3) providing a parallel interferometer having a probe beam and a reference beam;

(4) propagating the thermal-wave established in said material sample first layer through the second layer and to the third layer, the third layer being selected to induce an optical phase-shift in the probe beam of said interferometer, the optical phase-shift resulting from a variation in optical properties of said third layer as the thermal-wave is propagated in said third layer;

(5) directing the probe beam of the interferometer towards the thermooptical phase-shift element such that the probe beam enters through the third layer, reflects on the second layer, and returns to the interferometer, through the third layer, with an optical phase-shift;

(6) parallelly detecting with the interferometer the phase-shift in the phase-shifted probe beam, and establishing an interferogram by comparing at once at a plurality of points the phase-shifted probe beam and the reference beam; and (7) parallelly recording the interferogram which contains the thermal wave image information of the sample from which the thermal wave image is obtained.

* * * * *